United States Patent
Feldchtein et al.

(10) Patent No.: US 7,227,629 B2
(45) Date of Patent: Jun. 5, 2007

(54) CALIBRATION TOOL FOR AN OPTICAL MEASURING DEVICE WITH AN OPTICAL FIBER PROBE

(75) Inventors: Felix I. Feldchtein, Cleveland, OH (US); J. Lloyd Breedlove, Mooresville, NC (US); Stephanie A. S. Harrington, Mentor, OH (US)

(73) Assignee: Imalux Corporation, Cleveland, OH (US)

( * ) Notice: Subject to any disclaimer, the term of this patent is extended or adjusted under 35 U.S.C. 154(b) by 44 days.

(21) Appl. No.: 11/152,936

(22) Filed: Jun. 15, 2005

(65) Prior Publication Data

US 2005/0275836 A1 Dec. 15, 2005

Related U.S. Application Data

(60) Provisional application No. 60/579,631, filed on Jun. 15, 2004.

(51) Int. Cl.
*G01J 1/10* (2006.01)
(52) U.S. Cl. ..................... 356/243.1; 600/310; 600/331
(58) Field of Classification Search ............. 356/243.1, 356/51, 236, 448, 364, 369, 39–41, 479, 356/477; 250/228, 340, 227.19; 600/331, 600/310
See application file for complete search history.

(56) References Cited

U.S. PATENT DOCUMENTS

| | | | |
|---|---|---|---|
| 3,470,320 A | 9/1969 | Pike et al. | |
| 3,941,927 A | 3/1976 | Russell | |
| 4,047,032 A | 9/1977 | Judge et al. | |
| 4,050,450 A | 9/1977 | Polanyi et al. | |
| 4,236,784 A | 12/1980 | Palmer | |
| 4,322,164 A | 3/1982 | Shaw et al. | |
| 4,744,656 A | 5/1988 | Moran et al. | |
| 5,123,738 A | 6/1992 | Yonemura | |
| 5,305,744 A | 4/1994 | Pfeiffer et al. | |
| 5,741,441 A | 4/1998 | Watts et al. | |
| 5,782,757 A * | 7/1998 | Diab et al. ................... | 600/323 |
| 5,866,894 A | 2/1999 | Bard et al. | |
| 6,108,096 A * | 8/2000 | Ushio et al. ................. | 356/432 |

(Continued)

OTHER PUBLICATIONS

International Search Report for International Application No. PCT/US05/21210, International Filing Date: Jun. 15, 2005.

*Primary Examiner*—Gregory J. Toatley, Jr.
*Assistant Examiner*—Tri Ton
(74) *Attorney, Agent, or Firm*—Tucker Ellis & West LLP

(57) ABSTRACT

An optical measurement device calibration tool includes an optical probe suitable for calibrating various optical imaging devices, for example, low coherence reflectometers and optical coherence tomography devices. In a preferred embodiment the calibration tool comprises a container containing a calibration substance with stable optical scattering and absorption properties. The calibration substance includes a gel, paste or grease substance and is covered a protective seal, which is at least partially transparent providing optical contact between the optical probe and the calibration substance. The protective seal is covered with a viscous complementary material. Another protective seal made at least partially removable is placed above the viscous complementary material and may serve as a cover for the container. The calibration tool maintains the advantages of calibration tools using liquids and solid states as calibration substance and is more cost-effective and more convenient for calibrating optical measuring devices such as in medical applications.

21 Claims, 1 Drawing Sheet

U.S. PATENT DOCUMENTS

| | | |
|---|---|---|
| 6,226,541 B1 | 5/2001 | Eppstein et al. |
| 6,445,939 B1 | 9/2002 | Swanson et al. |
| 6,608,684 B1 | 8/2003 | Gelikonov et al. |
| 6,615,062 B2 | 9/2003 | Ryan et al. |
| 6,673,315 B2 * | 1/2004 | Sheridan et al. ............. 422/50 |
| 6,675,035 B1 | 1/2004 | Grable et al. |
| 6,810,279 B2 | 10/2004 | Mansfield et al. |
| 2005/0180962 A1 * | 8/2005 | Raz et al. ................ 424/93.45 |

* cited by examiner

CALIBRATION TOOL FOR AN OPTICAL MEASURING DEVICE WITH AN OPTICAL FIBER PROBE

CROSS-REFERENCE TO RELATED APPLICATIONS

This application is based on and claims priority to provisional U.S. patent application Ser. No. 60/579,631, which was filed on Jun. 15, 2004.

FIELD OF THE INVENTION

This invention relates to optical calibration, in particular, to a tool used for calibration of an optical measurement device having an optical probe, and can be used for calibrating various optical imaging devices, for example, low coherence reflectometers and devices for optical coherence tomography applied for medical diagnostics including in vivo or in vitro diagnostics, as well as for industrial diagnostics.

BACKGROUND OF THE INVENTION

Optical coherence tomography (OCT) is a rapidly developing high spatial resolution optical imaging modality. It uses low coherence interferometry for depth discrimination in turbid media. OCT creates two and three-dimensional maps of optical backscattering in turbid media. Since different components of biotissues scatter and absorb light differently and light scattering is also dependent on tissue localization and condition, OCT can provide valuable diagnostic information and can be used as a medical diagnostic imaging and therapy guidance tool. OCT can also be used for non-destructive evaluation of materials and composites, when penetration depth and contrast are sufficient.

Another optical imaging modality based on light scattering is laser confocal microscopy. It uses a different physical principle—(tight focusing instead of coherence gating in OCT) to selectively receive light backscattered from only small spatial area and reject diffuse scattering from all other areas. However, a confocal microscopy image is also no more than two or three-dimensional map of optical backscattering.

A combination of OCT and confocal microscopy, known as optical coherence microscopy (OCM), is a powerful tool for enhanced penetration depth, ultrahigh resolution. This technique requires spatial localization of a received backscattering signal, achieved by simultaneous application of coherence gating and tracking focus with high numerical aperture, moving synchronously with the coherence gate.

All known implementations of these optical modalities can exhibit dependence of the absolute optical backscattering signal from time and environmental conditions. A few examples include temperature and pressure parameter dependence of the optical elements and optical radiation sources, as well as aging of abovementioned optical elements. Also, the acquired spatial profiles of optical scattering can be influenced by imperfectness of scanning mechanisms and those mechanisms also can experience aging and dependence from environmental conditions. These spatial profiles can be specific for some materials, or biotissues location, or tissue pathological conditions. Therefore, separation between a "true" scattering spatial profile and artifacts induced by these factors is important.

For some applications, the absolute level of an optical backscattering signal in OCT is a characteristic of a specific material, or medical condition in biotissues and their components. All of the above shows the need for a tool for optical backscattering calibration or characterization. Ideally, such a tool should have stable and known optical absorption and scattering coefficients, with minimal dependence of such coefficients on time and environmental conditions. Homogeneous and isotropic spatial distribution of optical properties of the tool can greatly facilitate reliable measurement of "true" spatial scattering profiles by acquiring a test profile/image from the tool and using this test profile to quantify and correct above mentioned artifacts.

Another example of optical technologies using optical calibration tools with known optical scattering and absorption is spectroscopy, including fluorescent and absorption spectroscopy, and differential absorption optical devices.

Prior art optical calibration tools are known to use solid state calibration material. For example, U.S. Pat. No. 4,047,032 describes using ceramic as a calibration material, which preferably includes alumina for obtaining necessary optical properties. Other examples of calibration tools using solid state calibration material can be found in U.S. Pat. No. 4,322,164 and U.S. Pat. No. 5,305,633. However, solid state calibration material typically has some anisotropy and also it is more difficult to provide a stable optical contact between a solid calibration material and an optical probe. In many cases, the optical probes are hermetically sealed, being intended to be in contact with the sample, including human or animal biotissue or fluid.

It is also common to use suspensions of micro particles, including latex microspheres and intralipid solutions for optical scattering calibration as described in U.S. Pat. No. 4,744,656, in U.S. Pat. No. 5,123,738, or in U.S. Pat. No. 6,615,062. However these suspensions are not stable and exhibit sedimentation and coagulation. They are also expensive.

U.S. Pat. No. 5,741,441 teaches the use of a non-liquid scatter standard which comprises a normal cuvette filled with a clear silicon rubber gel in which effective light scattering amounts of inorganic particles are suspended. The calibration material taught by this patent exhibits rather stable optical properties, but the calibration tool is not convenient for calibrating optical measuring devices intended for use in medical applications.

A calibration tool for an optical measurement device having an optical probe which is more cost-effective and more convenient in medical applications, while exhibiting stable optical properties is therefore desirable and provided by this invention.

DISCLOSURE OF THE INVENTION

The present invention discloses herein the use of a calibration tool for an optical measurement device having an optical probe, which maintains the advantages of calibration tools using liquids and solid states as calibration substance and is more cost-effective and more convenient for calibrating optical measuring devices intended for use in medical applications.

According to the invention a calibration tool for an optical measurement device with an optical probe comprises a container, which is filled at least partially with a calibration substance with stable optical scattering and absorption properties. The container includes a first protective seal, which is at least partially transparent. The first protective seal has a first surface and a second surface, the first surface of the first protective seal being in optical contact with the calibration substance. The second surface of the first protective seal allows for an optical contact with the optical probe of the optical measurement device.

The calibration substance is preferably viscous. The first protective seal is preferably pliable and can be made as a polymer membrane.

In one embodiment the calibration substance includes a gel substance; in another embodiment the calibration substance includes a paste substance; in still another embodiment the calibration substance includes a grease substance. The grease substance may include a high vacuum grease substance.

The second surface of the first protective seal may be covered with a viscous complementary material. The viscous complementary material can include one of the following: a gel substance, a paste substance, a grease substance, or a wetting agent.

In a different embodiment the container further includes a second protective seal, which is made at least partially removable. The second protective seal has a first surface, which faces the second surface of the first protective seal, and a second surface. The second surface of the second protective seal may serve as a cover for the container. Accordingly, the second protective seal may be made as a safety cap.

In another embodiment the container may additionally include a removable safety cap. In a preferred embodiment the container is be made disposable.

It should be understood that the materials and examples are illustrative only and not intended to be limiting. Other features and advantages of the invention will be apparent from the following detailed description, and from the claims.

DETAILED DESCRIPTION OF THE INVENTION

Figure 1:
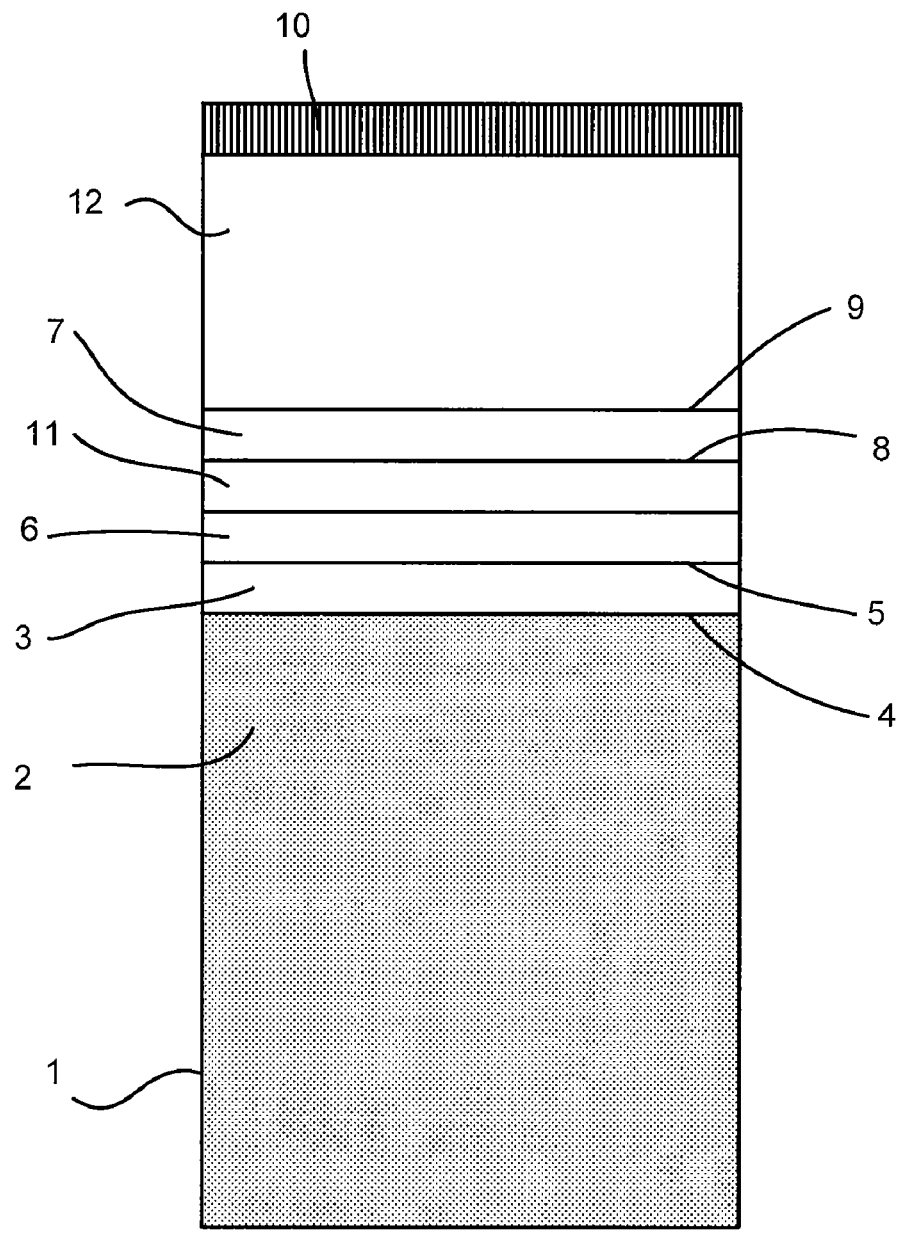
FIG. 1 is a cross section of a calibration tool for an optical measurement device according to one embodiment of the invention.

Referring to FIG. 1 a calibration tool for an associated optical measurement device with an associated optical probe includes a container 1, which is filled at least partially with a calibration substance 2. The container 1 can be made of any solid material. However, it should preferably be convenient and cost effective to manufacture the container from plastic. In a preferred embodiment the calibration substance 3 is a viscous, amorphous substance with stable optical scattering and absorption parameters. Possible implementations include suitable grease, paste, cream or gel substance or a combination of any of these substances. The grease substance may include a high vacuum grease substance. Such substances not being solid, therefore don't have internal mechanical tension and the associated optical anisotropy. They provide a good and stable optical coupling with sealed optical probes in addition, high viscosity prevents light scattering particles from coagulation and precipitation and provides more stable optical properties without agitation required for the low-viscosity liquids.

The calibration substance 2 should preferably be biocompatible and non-toxic to avoid hazardous action for a patient due to an accidental contact of the calibration substance 2 with the associate optical probe, when the calibration tool is used for calibration or quality control of an associated medical device before a medical procedure. In addition to the biocompatibility requirement, the container includes a protective seal, shown in FIG. 1 as a first protective seal 3, which is pliable and at least partially transparent. The associated optical probe of the associated optical measurement device (not shown in the drawing), contacts the calibration substance 2 via the first protective seal 3. The first protective seal 3 has a first surface 4 and a second surface 5, the first surface 4 of the first protective seal 3 being in optical contact with the calibration substance 2. The second surface 5 of the first protective seal 3 allows for an optical contact with the associated optical probe of the associated optical measurement device. In a preferred embodiment the first protective seal 3 is pliable and made as a polymer membrane.

To improve optical contact between the associated optical probe and first protective seal 3 the second surface 5 of the first protective seal 3 is covered with a viscous complementary material 6. The viscous complementary material 6 is capable of including, for example and without limitation, a gel substance, or a paste substance, or a grease substance, or a wetting agent. The viscous complementary material 6 is also capable of including a combination of above mentioned substances. For biomedical applications, the complementary material 6 should be biocompatible and non-toxic. It is also desirable that refraction indexes of the first protective seal 3 and complementary material 6 be close to the refraction index of optical probe window material (if the probe has a window) for better optical coupling. However, the later is not absolutely necessary since reflection loss is small for most plastic materials in contact with glass and stable for any pair of materials.

In the embodiment of FIG. 1 the container 1 includes a second protective seal 7, which is made at least partially removable. The second protective seal 7 has a first surface 8, which faces the viscous complementary material 6, and a second surface 9. The second surface 9 of the second protective seal 7 may serve as a cover for the container 1 or it may be made as a safety cap. In the embodiment of FIG. 1 the container 1 includes a removable safety cap 10.

In the exemplary embodiment shown in FIG. 1, the second seal 7 is separated from the complementary material 6 by a first air gap 11. Further, in this embodiment, the safety cap 10 is separated from the second seal 7 by a second air gap 12. As will be recognized by those skilled in the art, the air gaps 11, 12, are optional. It will be apparent to a skilled artisan that the second seal 7 may directly contact with the complementary material 6. Also, the safety cap 10 may directly contact with the second seal 7. Other suitable embodiments of the calibration tool of the subject application are capable of being employed without departing from the scope of the present invention.

Since very important OCT/CM/OCM applications are in the biomedical area, a preferred embodiment would be to provide a sterile calibration tool. The container 1 can be single-use and disposable.

Reliable theoretical calculation of optical properties is impractical in most cases, and therefore most of calibration substances need calibration and characterization. It is economically beneficial to perform this operation for a sample of a bulk lot of the substance 2, then dispense it to small containers and have a substantial amount of calibrated product from one set of measurements. The measurements may include any application-relevant properties as optical total or angle-resolved scattering at given wavelength, total optical extinction at given wavelength (including scattering and absorption), differential absorption or extinction at given pair of wavelengths or spectral/angular/polarization dependencies of these coefficients. Naturally a calibration procedure can also include assessment of aging of the calibration tool (accelerated or natural) and influence of environmental conditions.

To perform a calibration procedure using the calibration tool of the invention shown in FIG. 1 the safety cap 10 is first removed. Then the second seal 7 is at least partially removed to allow for an optical contact between the associated optical probe of the associated optical measurement device and the calibration substance 2. The associated optical probe of the associated optical measurement device (not shown in the drawing) is inserted into the container 1, the associated optical probe being brought into contact with the complementary material 6. Thus an optical contact is established between the associated optical probe and the calibration substance 2 through the complementary material 6 and the first seal 3.

For most applications, the calibration tool should have optical properties within some predefined range. The preferred range of refractive index is 1.3 to 1.5. The preferred range of optical absorption is 0–0.5 cm$^{-1}$, and scattering between 0.1–1 cm$^{-1}$. In one exemplary embodiment, a calibration tool is provided with negligible absorption and optical scattering similar to those produced by biotissues. Another example is a calibration tool with negligible (at OCT/OCM spatial scale, i.e. for several millimeter depth) optical extinction, yet producing sufficient backscattering signal, which can be measured with high signal to noise ratio. This situation is technically feasible and particularly convenient for factory calibration, testing and alignment of OCT/OCM devices, as well as for user-performed quality control and scattering profile precalibration. In particular it was experimentally found that silicone high vacuum grease (produced, for example, by Dow Corning) possesses all these above mentioned properties. In addition it is chemically inert, non-toxic and very environmentally stable. The preferred high vacuum grease has a chemical composition including 7–13% of amorphous silica, 60% of Polydimethylsiloxane, and −7–13% of hydroxyterminated Dimethyl siloxane. However, it should be appreciated that the present invention is not limited to any specific composition. It will be appreciated that any suitable composition could be employed without departing from the invention.

In cases when a specific combination of scattering and absorption properties is not readily available in a single substance or compound, the calibration tool can be prepared from several components.

The methods of using the calibration tools can be different. One method can include placing an optical probe into the container 1 with the calibration substance 2 and acquiring a test image or spatial profile. Then, if parameters of the acquired image or profile are not within the acceptance range, a manual adjustment can be made. Alternatively, a software routine can be embedded in the optical measurement device and then this routine can control image or profile acquisition and performing adjustment of the optical measurement device until device parameters will reach the optimal value or, if the optical measurement device is not (completely or partially) adjustable, the software routine can determine numerical coefficients needed to convert raw signal readings to reliable brightness or scattering profile or extinction parameters or differential absorption/concentration measurements parameters.

What is claimed is:

1. A calibration tool for an associated optical measurement device with an associated optical probe, comprising:
   a container;
   a calibration substance with stable optical scattering and absorption properties; and
   a first protective seal;
   wherein the container is filled at least partially with the calibration substance;
   wherein the first protective seal is at least partially transparent; and
   wherein the first protective seal has a first surface, which is in optical contact with the calibration substance, and a second surface, which allows for an optical contact with an associated optical probe of an associated optical measurement device.

2. The calibration tool according to claim 1, wherein the calibration substance is viscous.

3. The calibration tool according to claim 1, wherein the first protective seal is pliable.

4. The calibration tool according to claim 3, wherein the first protective seal is made as a polymer membrane.

5. The calibration tool according to claim 1, wherein the calibration substance includes a gel substance.

6. The calibration tool according to claim 1, wherein the calibration substance includes a paste substance.

7. The calibration tool according to claim 1, wherein the calibration substance includes a grease substance.

8. The calibration tool according to claim 7, wherein the grease substance includes a high vacuum grease substance.

9. The calibration tool according to claim 1, wherein the second surface of the first protective seal is covered with a viscous complementary material.

10. The calibration tool according to claim 9, wherein the viscous complementary material includes a gel substance.

11. The calibration tool according to claim 9, wherein the viscous complementary material includes a paste substance.

12. The calibration tool according to claim 9, wherein the viscous complementary material includes a grease substance.

13. The calibration tool according to claim 9, wherein the viscous complementary material includes a wetting agent.

14. The calibration tool according to claim 1, wherein the container is disposable.

15. A calibration tool for an associated optical measurement device with an associated optical probe, comprising:
   a container;
   a calibration substance with stable optical scattering and absorption properties;
   a first protective seal which is at least partially transparent; and
   a second protective seal;
   wherein the container is filled at least partially with the calibration substance;
   wherein the first protective seal has a first surface, which is in optical contact with the calibration substance, and a second surface, which allows for an optical contact with an associated optical probe of an associated optical measurement device;
   wherein the second protective seal has a first surface facing the second surface of the first protective seal, and a second surface; and
   wherein the second protective seal is made at least partially removable.

16. The calibration tool according to claim 15, wherein the calibration substance includes a grease substance.

17. The calibration tool according to claim 15, wherein the second protective seal is made as a safety cap.

18. The calibration tool according to claim 15, wherein the container is disposable.

19. The calibration tool according to claim 15, wherein the second surface of the first protective seal is covered with a viscous complementary material.

20. The calibration tool according to claim 15, wherein the second surface of the second protective seal serves as a cover for the container.

21. The calibration tool according to claim 15, wherein the container further includes a removable safety cap.

* * * * *